United States Patent
Amthor et al.

(10) Patent No.: US 10,426,974 B2
(45) Date of Patent: Oct. 1, 2019

(54) TREATMENT PLANNING SYSTEM

(71) Applicants: KONINKLIJKE PHILIPS N.V., Eindhoven (NL); SUNNYBROOK HEALTH SCIENCES CENTRE, Toronto, Ontario (CA)

(72) Inventors: Thomas Erik Amthor, Hamburg (DE); Falk Uhlemann, Hamburg (DE); SHyam Bharat, Arlington, MA (US); Ehsan Dehghan Marvast, New York, NY (US); Cynthia Ming-Fu Kung, New York, NY (US); Ananth Ravi, Toronto (CA); Jochen Kruecker, Washington, DC (US)

(73) Assignees: KONINKLIJKE PHILIPS N.V., Eindhoven (NL); SUNNYBROOK RESEARCH INSTITUTE (SRI), Toronto (CA)

( * ) Notice: Subject to any disclaimer, the term of this patent is extended or adjusted under 35 U.S.C. 154(b) by 167 days.

(21) Appl. No.: 15/305,374

(22) PCT Filed: Mar. 23, 2015

(86) PCT No.: PCT/EP2015/056108
§ 371 (c)(1),
(2) Date: Oct. 20, 2016

(87) PCT Pub. No.: WO2015/169498
PCT Pub. Date: Nov. 12, 2015

(65) Prior Publication Data
US 2017/0043180 A1    Feb. 16, 2017

Related U.S. Application Data

(60) Provisional application No. 61/988,960, filed on May 6, 2014.

(30) Foreign Application Priority Data

Jun. 4, 2014 (EP) .................................. 14171113

(51) Int. Cl.
*A61N 5/10* (2006.01)

(52) U.S. Cl.
CPC ........... *A61N 5/103* (2013.01); *A61N 5/1027* (2013.01); *A61N 2005/1041* (2013.01)

(58) Field of Classification Search
CPC .. A61N 5/1007; A61N 5/1031; A61N 5/1039; A61N 2005/1041; A61N 5/1027; A61N 5/103
See application file for complete search history.

(56) References Cited

U.S. PATENT DOCUMENTS 6,027,446 A * 2/2000 Pathak ................ G01S 7/52036
600/439
6,200,255 B1 3/2001 Yu
(Continued)

*Primary Examiner* — Christine H Matthews

(57) ABSTRACT

The generation of a pattern and for an adaptation to the specific geometry requires a lot of manual work. The workflow for the clinician is simplified during treatment planning. A treatment planning system is configured for determining a set of catheter or needle insertion positions to be used during treatment. The treatment planning system includes an image providing module for providing a medical image from which at least one treatment target structure can be derived. Further the treatment planning system includes a pattern providing module for providing one or a set of standard patterns for catheter or needle insertion including a plurality of catheter or needle insertion positions. The catheter or needle positions relate to treatment positions in the at least one treatment target structure.

19 Claims, 3 Drawing Sheets

(56) References Cited

U.S. PATENT DOCUMENTS

| | | |
|---|---|---|
| 6,413,204 B1 | 7/2002 | Winkler et al. |
| 6,505,065 B1 | 1/2003 | Yanof et al. |
| 7,346,381 B2 | 3/2008 | Okerlund et al. |
| 8,465,407 B2 | 6/2013 | Lebovic et al. |
| 9,123,097 B2 | 9/2015 | Lee et al. |
| 9,259,155 B2 | 2/2016 | Bharat et al. |
| 10,245,447 B2 | 4/2019 | Amthor et al. |
| 2007/0078306 A1 | 4/2007 | Allison et al. |
| 2008/0214887 A1 | 9/2008 | Heanue et al. |
| 2009/0234175 A1 | 9/2009 | Maier |
| 2011/0153547 A1 | 6/2011 | McNutt et al. |
| 2012/0203053 A1 | 8/2012 | Kilby et al. |
| 2014/0018607 A1 | 1/2014 | Maier |

\* cited by examiner

TREATMENT PLANNING SYSTEM

CROSS-REFERENCE TO PRIOR APPLICATIONS

This application is the U.S. National Phase application under 35 U.S.C. § 371 of International Application Serial No. PCT/EP2015/056108, filed on Mar. 23, 2015, which claims the benefit of U.S. Application Ser. No. 61/988,960, filed on May 6, 2014 and European Patent Application No. 14171113.5, filed on Jun. 4, 2014. These applications are hereby incorporated by reference herein.

FIELD OF THE INVENTION

The invention relates to a system in the field of medical treatment planning.

BACKGROUND OF THE INVENTION

In the context of a typical medical intervention like brachy therapy a pre-plan is performed based on pre-procedural imaging (e.g. MRI, ultrasound, X-ray) data, wherein treatment target structures are delineated, together with one or more critical organs to avoid. Often during brachytherapy a grid comprising a plurality of orifices is used to guide the insertion of catheters or needles in such a way that the final catheter or needle position resembles the planned position as close as possible.

Positioning means are used to align the grid correctly relative to a patient. The positioning means could be connectable to the patient table. After the patient and grid are positioned, the position of the grid can be calibrated with a medical imaging system. After this, based on a predetermined dose constraints an intervention plan (e.g. a HDR/LDR brachy treatment plan, thermal ablation plan) can be calculated, which plan provides needle insertion positions required to deliver a dose distribution that fulfills the prescribed dose constraints. In this way the positions in the grid through which catheters or needles need to be inserted during treatment can be determined.

The generation of the pattern and the adaptation to the specific geometry requires a lot of manual work.

SUMMARY OF THE INVENTION

It is an object of the invention to simplify the workflow for the clinician during treatment planning.

This object is achieved by a treatment system as described in claim 1.

The invention is partly based on the insight of the inventors that while well-suited grid positions can be found and proposed to the clinician by modern treatment planning software, many physicians rely on standard patterns for catheter or needle insertion, standard patterns have proven to yield good and robust treatment results. The system according to the invention, takes into account this usual way of working of the physician and results in a substantially less time consuming way of planning.

By automatically providing the clinician with one or a set of standard patterns, catheter or needle insertion pattern provided will adhere to a clinician's idea of preferred symmetry and shape, while at the same time the workflow is simplified, because the standard pattern does not have to be generated automatically. Furthermore, the invention may aid less experienced clinicians with the selection of a clinical acceptable catheter or needle insertion pattern.

A standard pattern is predetermined prior to creation of the intervention plan. A standard pattern shows a certain degree of symmetry and/or resembles to a significant extent an insertion pattern, that a clinician experienced with these treatments would come up with if he was to create the catheter or needle insertion pattern manually. Furthermore, a standard pattern may be based on the clinician's insight on maximum and/or minimum catheters or needles to be used and/or needle or catheter density or distances to an edge of the treatment target structure and/or organ at risk. A standard pattern could be directly used after its selection or could be a starting point for (restrictive) optimization.

A set of standard patterns could be generated by analyzing the catheter or needle insertion patterns used by experienced clinicians. Alternatively, the treatment planning system could be configured to allow the clinician to create the set used by the pattern providing module himself. This is advantageous, since different clinics may use different standard patterns. By allowing the clinician to create the set himself he has more influence on the standard patterns, while the workflow remains simplified over the standard workflow, as in the standard workflow a lot of manual work is required for each individual patient for the generation of the pattern and for the adaptation to the specific geometry. Furthermore, the treatment planning system could be configured to allow addition or removal of standard patterns from the system. Also this allows the clinician to further optimize the system to his own preferences. The set of standard patterns could be saved in a database.

Alternatively, one or the set of standard patterns could be generated in a rule-based way based on the patient's treatment target and avoidance structures. This could be done on the fly, while the patient is already positioned on the patient support prior to the treatment.

An embodiment of the treatment planning system further comprises a module for enabling a selection of one or more catheter or needle insertion patterns from the set of standard patterns based on a comparison of a geometry of the standard patterns with at least one treatment target structure or based on a comparison of a treatment dose resulting from the standard patterns with a predetermined dose constraint. The treatment planning system is configured to provide the clinician with a projection of a set of standard catheter or needle insertion positions on the treatment target structure. The clinician is enabled to select a catheter or needle insertion position pattern from this set. Alternatively, the treatment system automatically selects one or more standard patterns which best match a geometry of the treatment target structure or for which a resulting treatment dose best matches a predetermined dose constraint. A best match of the geometry could for example be determined by investigating which standard insertion pattern or patterns give a good coverage of the treatment target structure, while not having catheter or needle positions outside the treatment target structure. A predetermined dose constraint could for example be a minimal dose given to a treatment area or a maximum dose given to a neighbouring organ at risk. An organ at risk is an organ that may be damaged during the treatment by the dose provided to the treatment target structure, e.g. for prostate treatment the rectum, urethra and bladder are organs at risk. Examples of indicators of dosimetric quality are the conformality index or the Vx (volume receiving x % of the prescribed dose) or the Dx (the minimum dose covering x % of the volume).

An embodiment of the treatment planning system is configured for enabling segmentation of one or more no-access zones. A no-access zone is a region where a needle cannot or should not enter or pass through. This could for example be a critical structure, like the urethra, that could be harmed by the catheter or needle. Furthermore, a no-access zone could be a region where the catheter or needle could not enter or pass through because of the patient's anatomy (e.g. due to the presence of bone) or because of the position of the patient relative to a patient support he is positioned on. Segmentation could be done automatically by the treatment planning system or by a user of the system. This embodiment is advantageous, because information on the location of a critical structure could be used for the selection of a standard pattern. For example, a typical critical structure in the prostate is the urethra, which one should avoid puncturing. Therefore, according to embodiments of the invention standard pattern which would result in puncturing of the urethra, are not selected.

An embodiment of the treatment planning system comprises a patient specific optimization module configured for adapting the standard patterns to a patient specific geometry of the treatment target structure by using a cost function. The optimization allows at least one of uniform scaling, shifting blocks of catheter or needle insertion positions, removing or adding a single catheter or needle insertion position, shifting of a single catheter or needle insertion position. The cost function comprises a penalty term for deviations of the pattern from the symmetry and/or shape of the standard pattern. In this way, standard patterns can be optimized to the individual patient, while still adhering to the clinician's idea of preferred symmetry and shape. The treatment planning system can be configured to perform optimization before and/or after the selection of one or more standard insertion patterns.

An embodiment of the treatment planning system is configured for enabling a user to influence the penalty term. This could be done by setting at least one of a maximum allowed scaling of the pattern in x, y or z direction, a maximum allowed number of catheter or needle insertion points to be moved individually, a penalty depending on the distance a single catheter is moved, a penalty for asymmetry of the pattern, a measure for overall deviation from the standard pattern, a maximum allowed total number of catheter or needle insertion positions that may be added and/or removed, a penalty depending on the distance of the catheter from the surface of the target, a penalty on a resultant dose distribution to prevent undercoverage and hotspots. In this way the user can influence the amount a pattern may deviate from a standard pattern.

An embodiment of the treatment planning system is configured to remove a catheter or needle insertion position from the standard pattern if a trajectory from the insertion point to the treatment position enters or passes through the no-access zone. This is advantageous, because in this way unfeasible catheter or needle insertion patterns are avoided.

According to an embodiment of the treatment planning system the treatment target structure is the prostate. The treatment planning system automatically selects a medical image slice comprising a mid-gland of the prostate and a plurality of standard patterns from the set of standard patterns is projected to the prostate mid-gland. The geometry of the prostate midgland is compared with the standard patterns. Based on the comparison one or more standard patterns are selected. This is advantageous, because focussing on one slice compared to a 3D volume will speed up the process.

According to a further embodiment of the invention the treatment planning system comprises a medical imaging unit (e.g. ultrasound, MRI, X-ray) configured for acquiring a medical image from the treatment target structure and for providing the medical image to the image providing module. The treatment planning system could further comprise a display which is configured for displaying a plurality of selected standard patterns for allowing a user for selecting a preferred catheter or needle insertion pattern from the plurality of selected standard patterns. Furthermore, the treatment planning system is configured for receiving a user input regarding a standard pattern selected by the user.

This invention is not limited to brachytherapy but could also be used for planning treatment with e.g. RF or HIFU needles. Furthermore, embodiments of the invention could be implemented as software as a stand-alone treatment planning system. Embodiments of the invention could also be used to upgrade an existing treatment planning system.

These and other aspects of the invention will be apparent from and elucidated with reference to the embodiments described hereinafter.

DETAILED DESCRIPTION OF THE INVENTION

Figure 1:
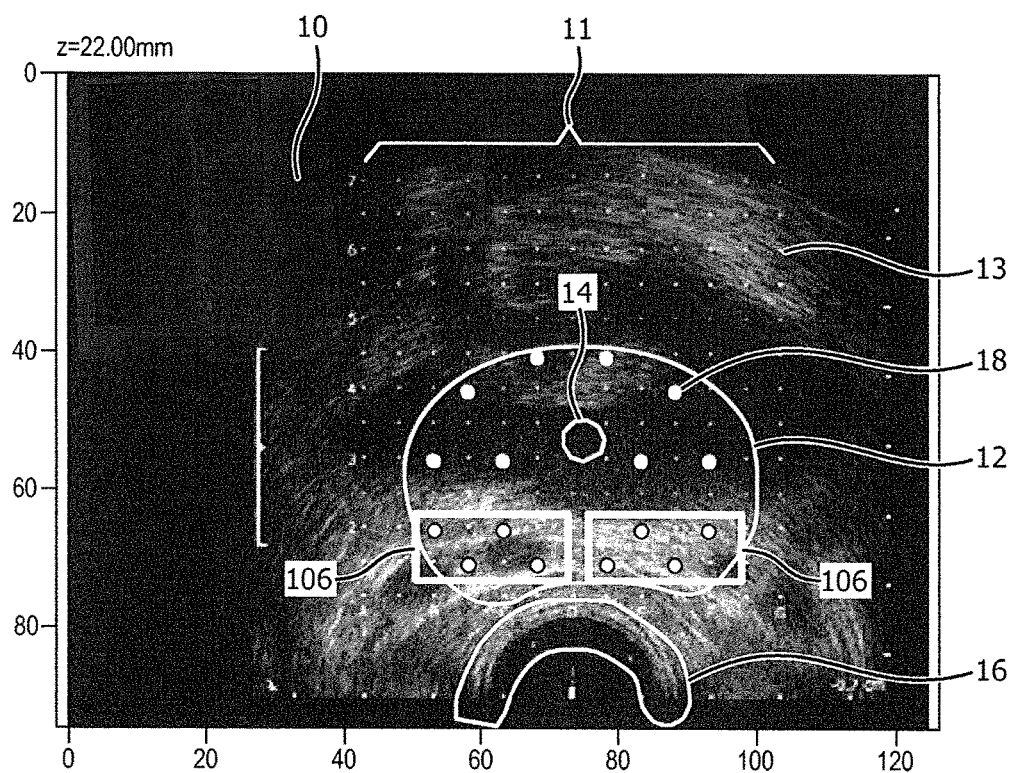
FIG. 1 shows an ultrasound image of the prostate.

FIG. 1 shows an ultrasound image 10 of the prostate 12. On top of the image the grid 11 is projected. The grid comprises a plurality of orifices 13. Several orifices are selected as catheter or needle insertion positions (e.g. 18). These catheter or needle insertion positions together form a standard pattern. As can be seen in FIG. 1, the catheter or needle insertion pattern is symmetric and resembles the geometry of the prostate 12. Furthermore, can be seen that some distance is kept between the urethra 14 and the surrounding catheter or needle positions (e.g. 18). In this way puncturing of the urethra with a catheter or needle can be prevented. Furthermore, in this way the treatment dose to the urethra can be limited, while applying a high treatment dose to the prostate. This will limit the chance of dose induced toxicity in the urethra. For the same reason, some distance is kept between the catheter or needle positions and the rectum 16.

Figure 2:
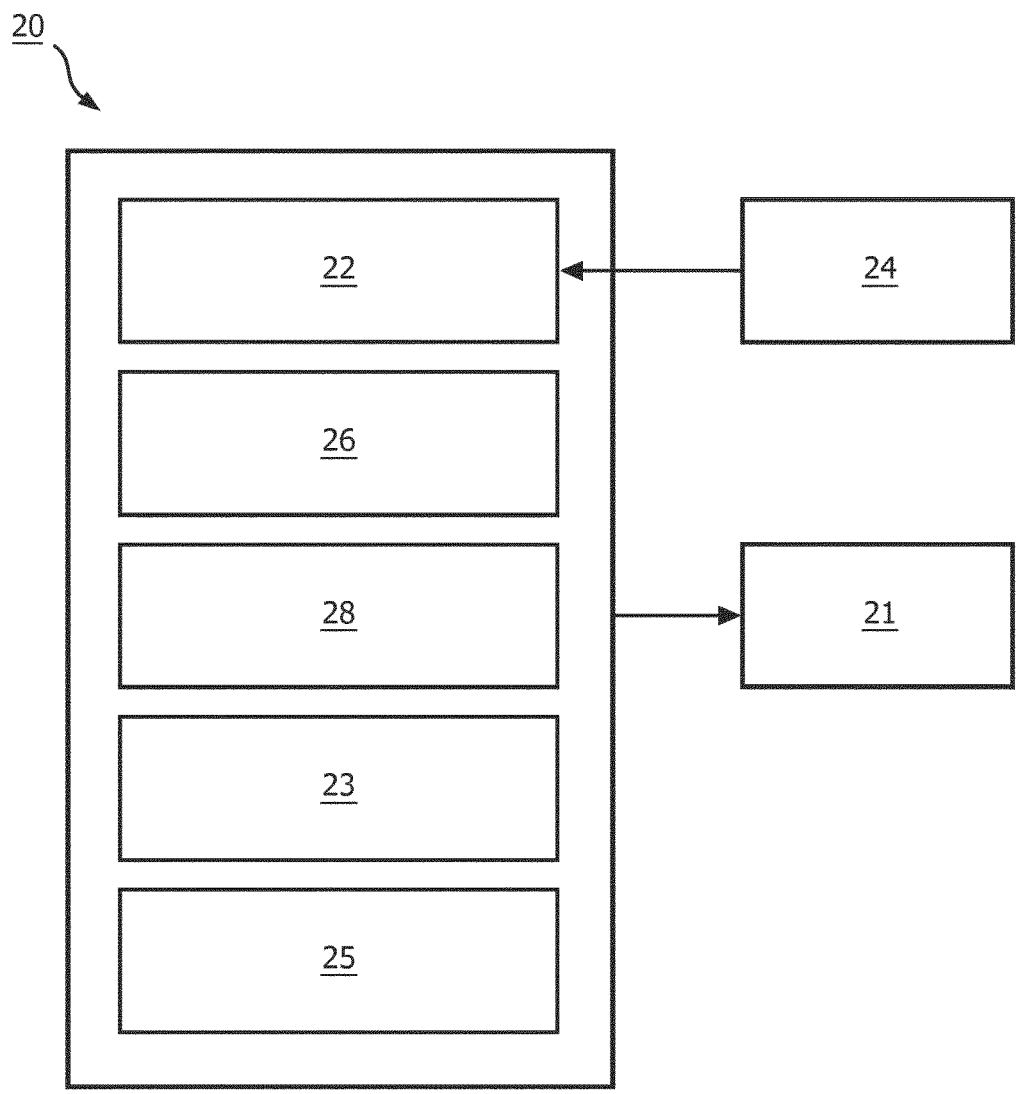
FIG. 2 schematically shows an embodiment of a treatment planning system.

FIG. 2 schematically shows an embodiment of a treatment planning system 20. The treatment planning system comprises an image providing module for providing a medical image from which at least one treatment target structure 12 can be derived. The treatment planning system could further comprise a medical imaging unit 24 (e.g. ultrasound, MRI, X-ray). The medical imaging unit is configured to provide images to the image providing module 22. Alternatively, the image providing module may load a medical image e.g. from a network, a patient database, USB stick. In this case the medical image may comprise a delineation of the treatment target structure 12. Such delineation may help for an automatic selection of one or more standard needle insertion patterns that best match a geometry of the target or which best fulfil predetermined dose constraints. Furthermore, the medical image may comprise one or more delineations of no-access zones for the catheter or needle (e.g. bone, urethra) or organs at risk, which need to be spared when applying dose to the treatment target structure. Also the treatment planning system may comprise a segmentation enabling module 26 which is configured for either automatically segmenting one or more structures in the medical image or enabling a user to segment structures in the medical image.

A pattern providing module 28 provides one or a set of standard patterns. The one standard pattern could be generated based on the patient's treatment target structure in a rule-based way. Rule-based generation of one or more standard patterns means that at least a symmetry rule is used for the generation of the one or more standard patterns. This could be done by setting a penalty on violation of symmetry and/or by addition and/or removal of needles or catheters in a symmetric way to the standard pattern. Furthermore, a maximum and/or minimum number of catheters or needles to be used can be set. Also distances between catheters/needles could optionally be set as well as distances between catheters or needles and the edge of the treatment target structure or a distance from a catheter or needle to an organ at risk. Furthermore, optionally a catheter or needle density can be set. This density could be adaptable for different states of disease and/or different sub-regions. The one or more standard patterns could be build by combination of sub patterns 106. An example of this for the prostate 12 could be for example the use of two substantially symmetric sub patterns 106 of 4 catheter and/or needle insertion positions below the urethra 14. This rule-base generated standard pattern could be directly used for catheter or needle insertion by the clinician or could be provided to the optimization module for further optimization.

The set of standard patterns could be provided to the module for enabling a selection 23 of one or more standard patterns based on a comparison of a geometry of the standard patterns with the at least one treatment target structure or based on a comparison of a resulting treatment dose resulting from the standard patterns with a predetermined clinical dose constraint. This selection could be done automatically by the treatment planning system (e.g. by determination of values for Vx or Dx or by determination of a conformality index). Alternatively, the user selects one or more standard patterns himself from the plurality of standard patterns provided by the pattern providing module. To this end the standard patterns are displayed on a display 21. A combination of the above mentioned options is also possible, e.g. the treatment planning system could be configured for automatically making a first selection of a plurality of standard patterns from which the user can make a final selection.

The treatment planning system may compute and output specific grid holes to be used for the catheters or needles in the standard pattern to obtain the optimal positioning of the chosen standard pattern. If multiple standard patterns are chosen, each pattern has its optimal position defined.

The treatment planning system could furthermore comprise a patient specific optimization module 25. The optimization allows at least one of uniform scaling, shifting blocks of catheter or needle insertion positions, removing or adding a single catheter or needle insertion position, shifting of a single catheter or needle insertion position. For optimization a cost function is used. The cost function comprises a penalty term for deviations of the pattern from the symmetry and/or shape of the standard pattern. Also the cost function could comprise a penalty term for deviations of the optimized dose distribution from the prescribed dose constraints. Furthermore, the optimization module could be configured for automatically removing catheter or needle insertion positions from a standard insertion pattern if catheter or needle insertion through this position would result in a catheter or needle trajectory to the treatment target structure which passes a no-access zone like a critical structure, or a region which cannot be reached e.g. due to the patient's anatomy or its position on the patient support. The treatment planning system can be configured to perform optimization before and/or after the selection of one or more standard insertion patterns.

Figure 3:
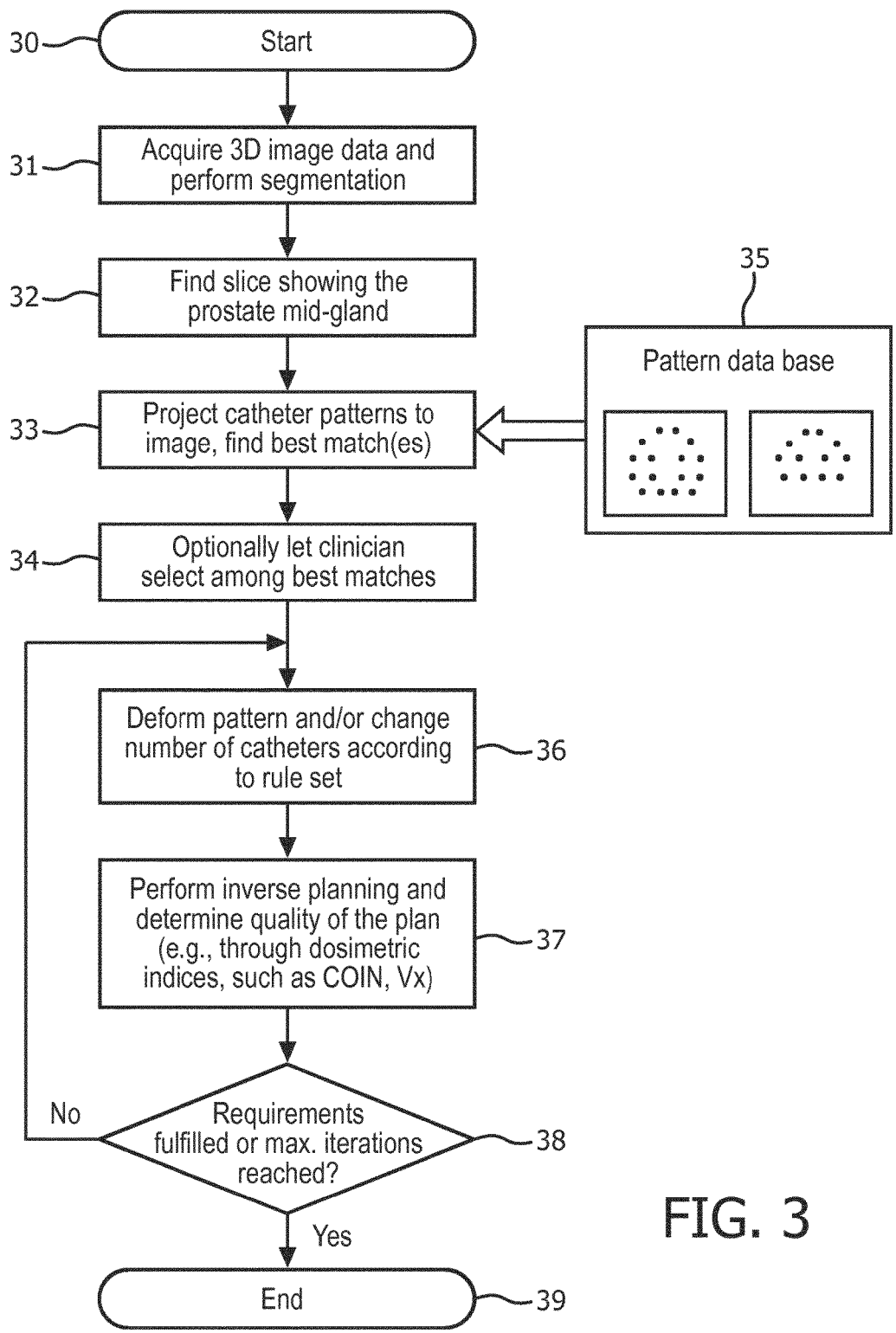
FIG. 3 diagrammatically shows an embodiment of the invention.

FIG. 3 diagrammatically shows an embodiment of the invention. First the patient is positioned on a table top and the grid is callibrated with the medical imaging unit 24. After this, execution of the treatment planning system is started 30. First the treatment planning system 20 executes the medical image unit to acquire medical images. According to this embodiment, these images are from the prostate. Furthermore, on these images a segmentation is performed 31. Based on the medical image and/or the segmentation the prostate mid-gland is found 32. This can for example be achieved by either determining an image slice containing the largest prostate cross section or simply choosing the middle slice of the segmented prostate. A plurality of standard patterns is taken from the set of standard patterns. This set can be available in a pattern database 35. Alternatively, one or more standard patterns may be generated rule-based. The plurality of standard insertion patterns are projected to the prostate mid-gland in order to find one or more best matches 33. Possibly, the user could select a standard pattern from a preselection made by the treatment planning system 34.

After the selection, the selected standard insertion pattern(s) could be deformed in a restricted way, such that required symmetry and shape remain 36. To further facilitate this the treatment planning system could be configured for enabling a user to modify the penalty term in the cost function, e.g. by allowing the user to set at least one of a maximum allowed scaling of the pattern in x, y or z direction, a maximum allowed number of catheter or needle insertion points to be moved individually, a penalty depending on the distance a single catheter is moved, a penalty for asymmetry of the pattern, a measure for overall deviation from the standard pattern, a maximum allowed total number of catheter or needle insertion positions that may be added and/or removed. After this inverse planning, as well known in the art, is performed. After this the quality of a resulting treatment plan is determined 37. This process is repeated until the resulting treatment plan fullfils a predetermined requirement or after a maximum number of iterations 38. After this the process is finished 39.

Whilst the invention has been illustrated and described in detail in the drawings and foregoing description, such illustrations and description are to be considered illustrative or exemplary and not restrictive; the invention is not limited to the disclosed embodiments and can be used for treatment planning within the field of medical treatment planning.

The invention claimed is:

1. A treatment planning system configured for determining a set of catheter or needle insertion positions to be used during treatment comprising:
    a computer processor configured to:
        receive a medical image of a patient including a treatment target structure to be treated;
        retrieve a set of predetermined standard patterns for catheter or needle insertion comprising a plurality of catheter or needle insertion positions, wherein the catheter or needle positions are positions from which inserted catheters or needles intersect the treatment target structure in a standardized patient; and
        adapt one or more standard patterns of the set of predetermined standard patterns to a geometry of the patient with the treatment target structure to be treated with the catheters or needles by using a cost function, wherein the cost function comprises a penalty term for deviations of the adapted one or more standard patterns from a symmetry and/or shape of the adapted one or more standard patterns.

2. The treatment planning system as claimed in claim 1, wherein the computer processor is further configured to:
select one or more catheter or needle insertion patterns from the retrieved set of predetermined standard patterns based on a comparison of a geometry of the predetermined standard patterns of the set with the treatment target structure or based on a comparison of a resulting treatment dose with a predetermined dose constraint.

3. The treatment planning system as claimed in claim 1, wherein at least one of the predetermined standard patterns are generated using rules based on a geometry of the treatment target structure.

4. The treatment planning system as claimed in claim 1, further including:
a database configured to store the set of predetermined standard patterns.

5. The treatment planning system as claimed in claim 1, wherein the computer processor is further configured to automatically determine if a trajectory from an insertion point of each inserted catheter or needle to a treatment position of the target structure of the patient would enter or pass through a no-access zone.

6. The treatment planning system as claimed in claim 1, wherein the one or more standard patterns of the set of predetermined standard patterns is adapted by at least one of:
uniform scaling of the one or more standard patterns of the set of predetermined standard patterns in at least one of x, y or z directions;
shifting blocks defining the catheter or needle insertion positions in at least one of x, y or z directions in a symmetric way;
shifting a single one of the catheter or needle insertion positions in an x, y or z direction; and
removing or adding a single catheter or needle insertion position from/to the one or more standard patterns of the set of predetermined standard patterns.

7. The treatment planning system as claimed in claim 6 configured for enabling a user to influence the penalty term by setting at least one of:
a maximum allowed scaling of the adapted one or more standard patterns in an x, y or z direction;
a maximum allowed number of catheter or needle insertion points to be moved individually;
a penalty depending on a distance a single catheter or needle is moved;
a penalty for asymmetry of the adapted one or more standard patterns;
a measure for overall deviation among the adapted one or more standard patterns;
a maximum allowed total number of corresponding predetermined catheter or needle insertion positions that may be added and/or removed;
a penalty depending on a distance between each of the catheters or needles and a surface of the treatment target structure; and
a penalty on a resultant dose distribution to prevent undercoverage and hotspots.

8. The treatment planning system as claimed in claim 5, wherein the computer processor is configured to:
remove one of catheter or needle insertion positions from the adapted one or more standard patterns if a trajectory from the insertion point to the treatment position enters or passes through the no-access zone.

9. The treatment planning system as claimed in claim 1, configured for planning treatment of a prostate, wherein the computer processor is further configured for performing the following steps:
automatically selecting a medical image slice comprising a mid-gland of the prostate;
projecting the one or more adapted standard patterns to the prostate mid-gland;
comparing a geometry of the one or more adapted standard patterns with the prostate mid-gland or based on a comparison of a resulting dose resulting from the one or more adapted standard patterns with a predetermined dose constraint; and
selecting one or more of the one or more adapted standard patterns which best conforms with a geometry of the prostate mid-gland or which treatment dose best matches the predetermined dose constraint.

10. The treatment planning system as claimed in claim 2, wherein the computer processor automatically selects a standard pattern from the set of standard patterns.

11. The treatment planning system as claimed in claim 6, wherein the computer processor is configured to select one or more of the one or more standard patterns after selecting the catheter or needle insertion positions.

12. The treatment planning system as claimed in claim 6, wherein the one or more standard patterns of the set of predetermined standard patterns is adapted based on dose constraints for the treatment target structure and at least one organ at risk.

13. The treatment planning system as claimed in claim 1, further comprising a medical imaging unit configured for acquiring a medical image of the treatment target structure and for providing the medical image to the computer processor.

14. The treatment planning system as claimed in claim 1, further comprising:
a display, which is configured for displaying the adapted one or more standard patterns of the set of standard patterns for allowing a user to select a preferred catheter or needle insertion pattern from the displayed standard patterns.

15. A treatment planning system configured for determining a set of catheter or needle insertion positions to be used during treatment comprising a computer or processor configured to:
receive a medical image from which at least one treatment target structure can be derived;
retrieve one or a set of predetermined standard patterns for catheter or needle insertion comprising a plurality of catheter or needle insertion positions, wherein the catheter or needle positions relate to treatment positions in the at least one treatment target structure; and
adapt one or more standard patterns to a patient specific geometry of the at least one treatment target structure by using a cost function, wherein the cost function comprises a penalty term for deviations of a resulting pattern from a symmetry and/or shape of the adapted one or more standard patterns.

16. The treatment planning system as claimed in claim 15, further including:
a database configured to store the one or the set of predetermined standard patterns, the computer or processor being configured to retrieve the one or more standard patterns from the database.

17. The treatment planning system as claimed in claim 16, further including:
a medical diagnostic scanner configured to generate the medical image received by the computer or processor.

18. A treatment planning method for determining a set of catheter or needle insertion positions to be used during treatment, comprising with the one or more processors of a treatment planning system:
receiving a medical image from which at least one treatment target structure can be derived;
retrieving one or a set of predetermined standard patterns for catheter or needle insertion comprising a plurality of catheter or needle insertion positions, wherein the catheter or needle positions relate to treatment positions in the at least one treatment target structure; and
adapting one or more standard patterns to a patient specific geometry of the at least one treatment target structure by using a cost function, wherein the cost function comprises a penalty term for deviations of a resulting pattern from a symmetry and/or shape of the adapted one or more standard patterns.

19. A non-transitory computer-readable medium carrying software configured to control a treatment planning system to:
receive a medical image from which at least one treatment target structure can be derived;
retrieve one or a set of predetermined standard patterns for catheter or needle insertion comprising a plurality of catheter or needle insertion positions, wherein the catheter or needle positions relate to treatment positions in the at least one treatment target structure; and
adapt one or more standard patterns to a patient specific geometry of the at least one treatment target structure by using a cost function, wherein the cost function comprises a penalty term for deviations of a resulting pattern from a symmetry and/or shape of the adapted one or more standard patterns.

* * * * *